United States Patent
Rai et al.

(10) Patent No.: US 11,090,528 B2
(45) Date of Patent: Aug. 17, 2021

(54) ROBOTIC PHYSICAL THERAPY SYSTEMS AND DATA ANALYSIS OF USER INTERACTIONS

(71) Applicant: The Trustees of the University of Pennsylvania, Philadelphia, PA (US)

(72) Inventors: Roshan Rai, Hellertown, PA (US); Michelle Jillian Johnson, Philadelphia, PA (US); Suneet Sharma, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 305 days.

(21) Appl. No.: 15/971,667

(22) Filed: May 4, 2018

(65) Prior Publication Data

US 2018/0318648 A1 Nov. 8, 2018

Related U.S. Application Data

(60) Provisional application No. 62/501,332, filed on May 4, 2017.

(51) Int. Cl.
*A63B 69/00* (2006.01)
*A63B 24/00* (2006.01)
(Continued)

(52) U.S. Cl.
CPC .......... *A63B 24/0087* (2013.01); *A61H 1/00* (2013.01); *A61H 1/02* (2013.01);
(Continued)

(58) Field of Classification Search
CPC .................................................. A63B 69/00
(Continued)

(56) References Cited

U.S. PATENT DOCUMENTS 5,407,402 A * 4/1995 Brown ................. A63B 21/154
482/111
5,993,356 A * 11/1999 Houston ............ A63B 21/0058
482/4
(Continued)

FOREIGN PATENT DOCUMENTS

EP 1732495 A2 12/2006
WO WO 2005/074371 A2 8/2005
(Continued)

OTHER PUBLICATIONS

Tang et al., "Measurement and Estimation of 3D Orientation using Magnetic and Inertial Sensors," Journal of Advanced Biomedical Engineering, pp. 135-143 (2015).
(Continued)

*Primary Examiner* — Kurt Fernstrom
(74) *Attorney, Agent, or Firm* — Jenkins, Wilson, Taylor & Hunt, P.A.

(57) ABSTRACT

Methods, systems, and computer readable media for analyzing robotic physical rehabilitation systems. In some examples, a method includes receiving user interaction data characterizing a user's interaction with a robotic rehabilitation system. The robotic rehabilitation system includes one or more robotic motion machines, a control system for controlling motors of the robotic motion machines, and one or more sensors for collecting the user interaction data while the user performs physical rehabilitation training using the one or more robotic motion machines. The method includes analyzing the user interaction data to track the user's past course of treatment and determine an action for the user's future course of treatment. The method includes sending one or more commands to the control system of the robotic rehabilitation system based on the action for the user's future course of treatment.

18 Claims, 5 Drawing Sheets

(51) Int. Cl.

| | |
|---|---|
| *G16H 20/30* | (2018.01) |
| *G16H 50/20* | (2018.01) |
| *A61H 1/00* | (2006.01) |
| *A63B 21/00* | (2006.01) |
| *A63B 71/06* | (2006.01) |
| *A61H 1/02* | (2006.01) |
| *G16H 40/63* | (2018.01) |
| *G16H 50/30* | (2018.01) |

(52) U.S. Cl.
CPC .... *A63B 21/00178* (2013.01); *A63B 24/0062* (2013.01); *A63B 24/0075* (2013.01); *A63B 71/0622* (2013.01); *G16H 20/30* (2018.01); *G16H 40/63* (2018.01); *G16H 50/20* (2018.01); *G16H 50/30* (2018.01); *A61H 2201/1659* (2013.01); *A61H 2201/5007* (2013.01); *A61H 2201/5061* (2013.01); *A63B 2024/0096* (2013.01); *A63B 2220/51* (2013.01); *A63B 2220/836* (2013.01); *A63B 2225/10* (2013.01)

(58) Field of Classification Search
USPC ............... 434/247, 255, 258; 482/4, 5, 8, 9; 700/245, 246, 248, 250
See application file for complete search history.

(56) References Cited

U.S. PATENT DOCUMENTS

| | | | |
|---|---|---|---|
| 6,666,799 B2 | 12/2003 | Hildebrandt et al. | |
| 6,921,351 B1* | 7/2005 | Hickman ............ | G06F 19/3481 482/8 |
| 7,556,590 B2* | 7/2009 | Watterson ............ | A63B 21/005 482/8 |
| 7,953,244 B2 | 5/2011 | Chang et al. | |
| 8,262,541 B2 | 9/2012 | Gravel et al. | |
| 9,144,709 B2 | 9/2015 | Reich et al. | |
| 9,173,612 B2 | 11/2015 | Craelius et al. | |
| 9,174,086 B1 | 11/2015 | Griggs et al. | |
| 9,248,071 B1 | 2/2016 | Benda et al. | |
| 9,272,186 B2* | 3/2016 | Reich ................ | A63B 24/0062 |
| 9,381,397 B2 | 7/2016 | Orgal | |
| 9,586,091 B2 | 3/2017 | Reich et al. | |
| 9,713,439 B1* | 7/2017 | Wu ........................ | A61B 5/112 |
| 9,750,978 B2 | 9/2017 | Nakashima et al. | |
| 9,877,682 B2 | 6/2018 | Craelius et al. | |
| 10,449,416 B2* | 10/2019 | Dalebout ........... | A63B 22/0007 |
| 10,524,728 B2* | 1/2020 | Kirby ................ | A61B 5/14542 |
| 2005/0159275 A1 | 7/2005 | Bullman et al. | |
| 2007/0135264 A1 | 6/2007 | Rosenberg | |
| 2008/0051256 A1* | 2/2008 | Ashby .................... | A63B 23/12 482/5 |
| 2008/0161733 A1* | 7/2008 | Einav .................... | A61H 1/0274 601/34 |
| 2010/0197462 A1 | 8/2010 | Piane, Jr. | |
| 2010/0312152 A1 | 12/2010 | Sarkodie-Gyan et al. | |
| 2011/0172058 A1 | 7/2011 | Deaconu et al. | |
| 2014/0336542 A1 | 11/2014 | Fu et al. | |
| 2015/0011361 A1 | 1/2015 | Boyette et al. | |
| 2015/0379239 A1 | 12/2015 | Basta et al. | |
| 2016/0007885 A1 | 1/2016 | Basta et al. | |
| 2016/0059140 A1* | 3/2016 | Bickel ..................... | A63H 11/20 446/353 |
| 2016/0081594 A1 | 3/2016 | Gaddipati et al. | |
| 2016/0183872 A1 | 6/2016 | Horst et al. | |
| 2017/0128769 A1 | 5/2017 | Long et al. | |
| 2018/0099184 A1 | 4/2018 | Eder | |

FOREIGN PATENT DOCUMENTS

| | | |
|---|---|---|
| WO | WO-2012/178171 A2 | 12/2012 |
| WO | WO-2017/040658 A1 | 3/2017 |

OTHER PUBLICATIONS

Kok et al., "An optimization-based approach to human body motion capture using inertial sensors," Proc. 19th World Congr. Int. Fed. of Autom. Control, pp. 79-85 (2014).

Chen, "Human Motion Analysis with Wearable Inertial Sensors," PhD Dissertation, University of Tennessee, 169 pages (2013).

Morton et al., "Pose Calibrations for Inertial Sensors in Rehabilitation Applications," 1st International Workshop on the e-Health Pervasive Wireless Applications and Services (eHPWAS'13), pp. 204-211 (Oct. 7-9, 2013).

Roetenberg et al., "Xsens MVN: Full 6DOF Human Motion Tracking Using Miniatrue Inertial Sensors," XSENS Technologies, pp. 1-9 (Apr. 3, 2013).

El-Gohary et al., "Shoulder and Elbow Joint Angle Tracking With Inertial Sensors," IEEE Transactions on Biomedical Engineering, vol. 59, No. 9, pp. 2635-2641 (Sep. 2012).

Font et al., "Development of a Virtual Humanoid Model Using the Denavit-Hartenberg Parameters as a Base for Visual Feedback Applications," Advances in Automation and Robotics, Lecture Notes in Electrical Engineering, vol. 1, pp. 639-646 (2012).

Prayudi et al., "Design and Implementation of IMU-based Human Arm Motion Capture System," 2012 International Conference on Mechatronics and Automation, pp. 670-675 (Aug. 2012).

El-Gohary et al., "Upper Limb Joint Angle Tracking with Inertial Sensors," 33rd International Conference of the IEEE EMBS, pp. 5629-5632 (Aug. 30, 2011-Sep. 3, 2011).

Yang et al., "A Calibration Process for Tracking Upper Limb Motion with Inertial Sensors," 2011 International Conference on Mechatronics and Automation (ICMA), pp. 618-623 (Aug. 7-10, 2011).

Hoffmann et al., "Automatic Calibration of a Motion Capture System Based on Inertial Sensors for Tele-Manipulation," Proceedings of 7th International Conference on Informations in Control, Automation and Robotics (ICINCO), 8 pages (Jun. 2010).

Morasso et al., "Desirable features of a "Humanoid" Robot-Terapist," 31st Annual International Conference of the IEEE EMBS, pp. 2418-2421 (Sep. 2009).

Nanda et al., "Design and evelopment of an Upper Extremity Motion Capture System for a Rehabilitation Robot," 31st Annual International Conference of the IEEE EMBS, pp. 7135-7138, (Sep. 2-6, 2009).

Zhou et al., "Human Motion Tracking for Rehabilitation—A survey," Biomedical Signal Processing and Control, vol. 3, Issue 1, pp. 1-18 (Jan. 2008).

Roetenberg, "Inertial and Magnetic Sensing of Human Motion," ISBN-13: 978-90-9020620-2, pp. 1-126 (2006).

Spong et al., "Robot Modeling and Control," First Edition, Wiley, 419 pages (2006).

Yun et al., "Design, Implementation, and Experimental Results of a Quaternion-Based Kalman Filter for Human Body Motion Tracking," IEEE Transactions on Robotics, vol. 22, No. 6, pp. 1216-1227 (Dec. 2006).

Zhou et al., "Inertial motion tracking of human arm movements in stroke rehabilitation," International Conference Mechatronics and Automation, vol. 3, No., pp. 1306-1311 (2005).

Murray et al., "A Mathematical Introduction to Robotic Manipulation," CRC Press, pp. 99-100 (1994).

* cited by examiner

ROBOTIC PHYSICAL THERAPY SYSTEMS AND DATA ANALYSIS OF USER INTERACTIONS

CROSS-REFERENCE TO RELATED APPLICATIONS

This application claims the benefit of U.S. Provisional Patent Application Ser. No. 62/501,332, filed May 4, 2017, the disclosure of which is incorporated herein by reference in its entirety.

TECHNICAL FIELD

This specification relates generally to robotic systems for physical rehabilitation.

BACKGROUND

Physical rehabilitation therapy is useful for many patients experiencing various kinds of illnesses. The issues influencing rehabilitation outcomes are complex; some examples of these issues are poverty, increase in health costs, short length of stays, insurance limitations, and physical constraints on therapist services (e.g., time). There is a substantial need for rehab services in various settings, but the supportive infrastructure is often inadequate. Robotic physical rehabilitation systems can compete with traditional therapies in terms of effectiveness while requiring less oversight from care providers. In many community-based settings, the patient population will vary, and therapists must treat a diversity of users with upper and lower limb deficits resulting from diagnoses such as stroke, spinal cord injury, Parkinson's, traumatic brain injury, and cerebral palsy. Robotic physical rehabilitation systems must have versatility to compete with traditional therapies in providing assessment and treatment for disability resulting from a diversity of diagnoses.

SUMMARY

This specification describes methods, systems, and computer readable media for analyzing robotic physical rehabilitation systems. In some examples, a method includes receiving user interaction data characterizing user's or users' interaction with a robotic rehabilitation system. The robotic rehabilitation system includes one or more robotic motion machines, a control system for controlling motors of the robotic motion machines, and one or more sensors for collecting the user interaction data while the user performs physical rehabilitation training using the one or more robotic motion machines. The method includes analyzing the user interaction data to track the user's past course of treatment and determine an action for the user's future course of treatment. In some examples, the method includes sending one or more commands to the control system of the robotic rehabilitation system based on the action for the user's future course of treatment. The method includes sending one or more commands to the control system of the robotic rehabilitation system based on the user's present action on one robotic motion machine to influence another user's future action on another robotic motion machine during competitive, collaborative or cooperative play. The methods and systems can, in some examples, help diagnose and quantify the level of impairment of the patient—and at a much faster rate than is feasible than through some conventional clinical means. The methods and systems can be used for, e.g., diagnostic purposes, therapy purposes, or both.

The subject matter described herein may be implemented in hardware, software, firmware, or any combination thereof. As such, the terms "function" or "node" as used herein refer to hardware, which may also include software and/or firmware components, for implementing the feature(s) being described. In some exemplary implementations, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

DETAILED DESCRIPTION

Figure 1:
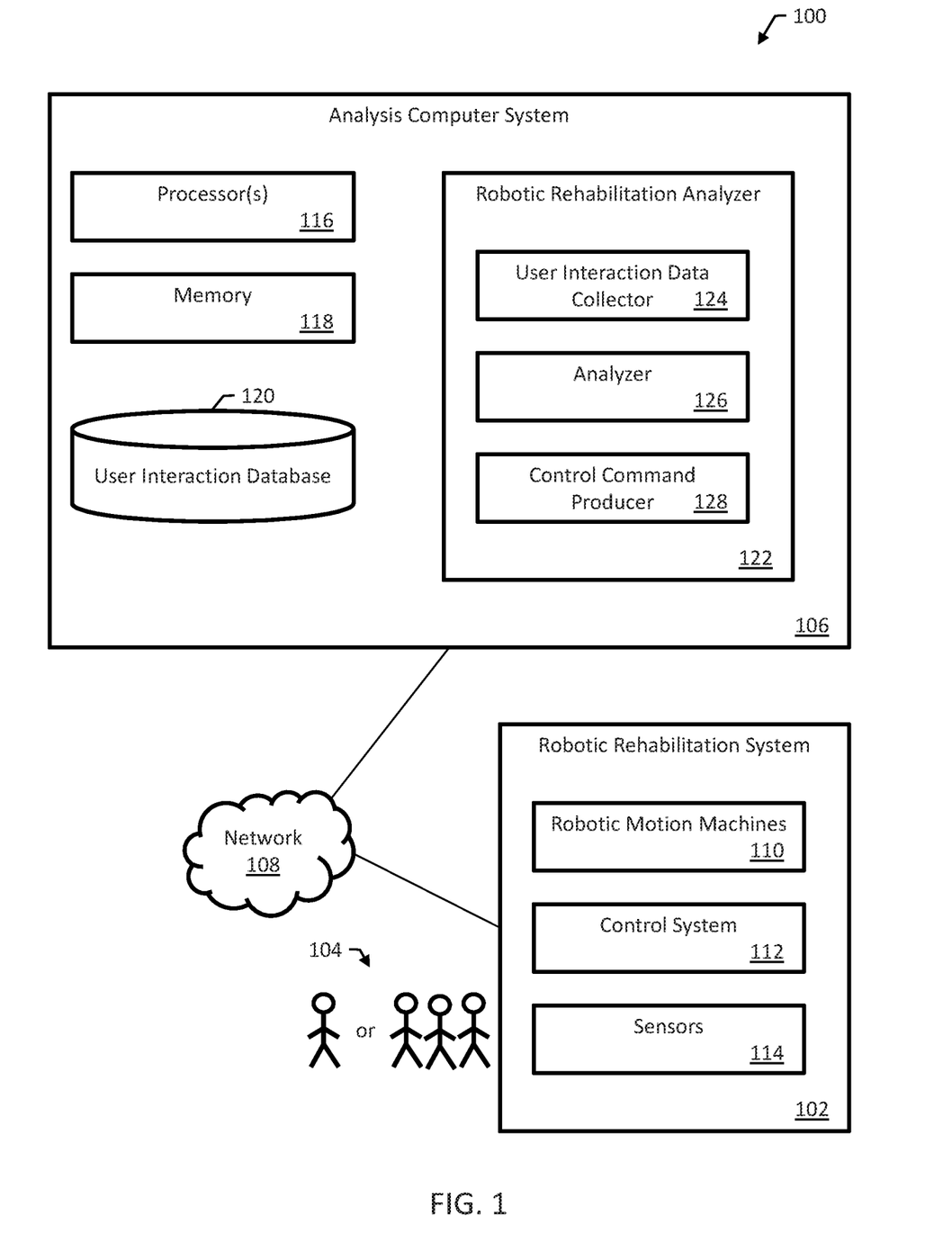
FIG. 1 is a block diagram of an example network environment for analyzing robotic physical rehabilitation systems.

FIG. 1 is a block diagram of an example network environment 100 for analyzing robotic physical rehabilitation systems. Network environment 100 includes an example robotic rehabilitation system 102 and one or more users 104 that perform physical rehabilitation training using robotic rehabilitation system 102. Network environment 100 also includes an analysis computer system 106 that communicates with robotic rehabilitation system 102 over a data communications network 108, e.g., the Internet.

Robotic rehabilitation system 102 includes one or more robotic motion machines 110, a control system 112 for controlling motors of the robotic motion machines 110, and one or more sensors 114 for collecting user interaction data while one or more users 104 perform physical rehabilitation training using the robotic motion machines 110. Sensors 114 can be, e.g., position sensors, or sensors embedded within or integrated within robotic motion machines 110 for measuring force and position at user contact surfaces of robotic motion machines 110. In some examples, sensors 114 include biometric sensors or a motion capture system, e.g., an inertial measurement unit (IMU) motion capture system for capturing the movement of user 104. In some examples, sensors 114 include one or more biometric sensors.

Analysis computer system 106 includes one or more processors 116 and memory 118 storing executable instructions for processors 116. Analysis computer system 106 also includes a user interaction database 120 for storing user interaction data. A robotic rehabilitation analyzer 122 is implemented on analysis computer system 106. Robotic rehabilitation analyzer 122 includes a user interaction data collector 124 for receiving user interaction data characterizing user 104's interaction with robotic rehabilitation system 102 and storing the user interaction data in the user interaction database 120.

Robotic rehabilitation analyzer 122 also includes an analyzer 126 for analyzing the user interaction data to track user 104's past course of treatment and to determine an action for user 104's future course of treatment. Robotic rehabilitation analyzer 122 includes a control command producer 128 for sending one or more commands to control system 112 based on the action for user 104's future course of treatment.

In some examples, analyzing the user interaction data includes determining diagnosis data or therapy data or both for user 104 based on the user interaction data and comparison data. The comparison data can be, e.g., previously recorded user interaction data or expected or average user interaction data for users at certain levels or stages of certain kinds of physical rehabilitation therapy. In some examples, analyzing the user interaction data includes determining, using comparison data one or more of: error data, rate of learning data, visuospatial performance data, working memory performance data, attention deficit data and force data.

In some examples, since users of the system may have deficits in the lower and/or upper extremities from a wide variety of diagnoses, the robotic rehabilitation analyzer 122 includes the ability to receive data users' medical history, therapy on motor and cognitive function and on-going performance data with gaming system.

In some examples, network environment 100 includes multiple users that perform physical rehabilitation training using robotic motion machines 110. For example, the users may take turns performing physical rehabilitation training. In some examples, robotic rehabilitation system 102 is a multi-user robotic physical rehabilitation gym having multiple component stations each having robotic motion machines, and the users may perform physical rehabilitation training at the same time. Robotic rehabilitation analyzer 122 can be configured for analyzing user interaction data from all of the users for any of various appropriate tasks, e.g., for producing commands for user-specific training or for producing aggregated data for trend analysis.

In some examples, robotic rehabilitation system 102 includes multiple passive only devices, i.e., devices that apply only resistance. In some other examples, robotic rehabilitation system 102 includes active only devices, i.e., devices that can apply assistance or resistance. In some examples, robotic rehabilitation system 102 includes active and passive devices.

In some examples, network environment 100 includes multiple robotic rehabilitation systems, e.g., as described further below with reference to FIG. 4. Robotic rehabilitation analyzer 122 can be configured for receiving user interaction data from the multiple robotic systems and analyzing user interaction data from all of the multiple robotic rehabilitation systems for any of various appropriate tasks, e.g., for producing commands for user-specific training or for producing aggregated data for trend analysis.

In some examples, control system 112 includes a display and one or more processors. Control system 112 can be configured, e.g., to provide feedback to user 104 using the display, so that control command producer 128 can send commands to alter the feedback provided to user 104. Control system 112 can be configured for interactive gaming with user 104 while user 104 performs physical rehabilitation training, e.g., as described further below with reference to FIGS. 5A-C. Control command producer 128 can send commands to alter the interactive gaming with user or users 104.

In some examples, control system 112 is configured for providing assistive and resistive haptic feedback to user 104 by controlling motors of the robotic motion machines. Control command producer 128 can send commands to alter the assistive and resistive haptic feedback.

In some examples, robotic rehabilitation system 102 is configured to use tele-tools to deliver effective therapeutic interventions. Mobile health tools can be integrated, e.g., into a graphical user interface (GUI), to configure the system such that a physician at a health center can evaluate and provide direct consultation to patients in remote settings.

Figure 2:
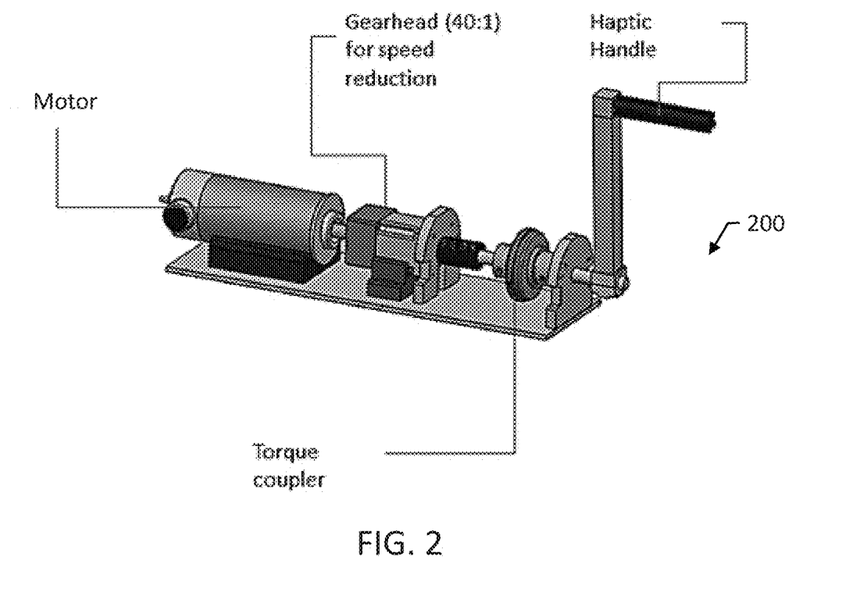
FIG. 2 illustrates an example robotic motion machine configured for providing assistive and resistive haptic feedback to a user.

FIG. 2 illustrates an example robotic motion machine 200 configured for providing assistive and resistive haptic feedback to a user. The robotic motion machine 200 includes a motor (e.g., a direct current (DC) electrical motor), a gearhead, a torque coupler, and a user contact surface (e.g., a haptic handle). The robotic motion machine 200, when different user interfaces are placed on it, is capable of allowing users to complete exercises with shoulder and elbow (upper limb) and exercises with hip and knee (lower limb) depending on orientation and placement (vertical or horizontal). It allows for adaptive forces up to, e.g., its 200N or an equivalent torque of 45 Nm at the end effector (crank arm) to be applied to the user to provide assistance or resistance in completing movement tasks. Assistance or resistance is created by controlling the torque motor and for safety the maximum forces can be limited by a torque limiter. The power supply needed to run the robotic motion machine may be untethered from a power grid and supplied within the physical rehabilitation gym or maybe tethered to a power grid. In some examples, the robotic motion machines 200 are configured to be used in regions where power grid access is low. In some examples, the power supply may be from a battery, a generator, or a solar grid.

Although FIG. 2 illustrates an example robotic motion machine 200, various other types of robotic motion machines can be used in physical rehabilitation training, and any appropriate type of robotic motion machine can be used in the systems and methods described in this specification.

Figure 3:
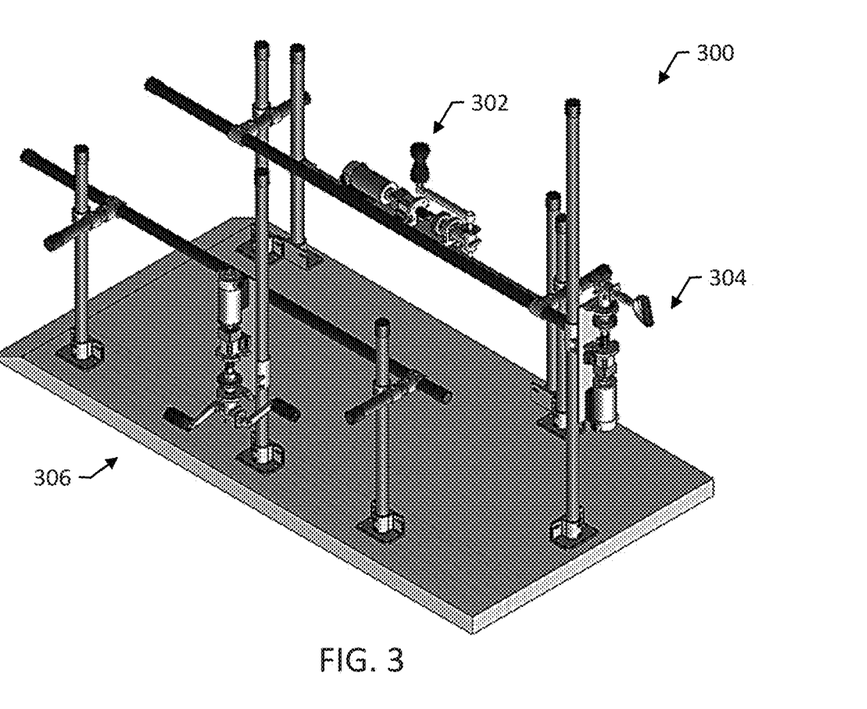
FIG. 3 illustrates an example robotic rehabilitation system configured with multiple robotic motion machines with different end-effector configurations to accommodate different upper limb orientations.

FIG. 3 illustrates an example robotic rehabilitation system 300 configured with multiple robotic motion machines 302, 204, and 306. The robotic rehabilitation system 300 can be used as a multi-user robotic physical rehabilitation gym, where each robotic motion machine is staged as a component station using physical structures such as parallel bars. In some examples, the robotic rehabilitation system 300 contains a central gait training station, one lower/upper limb cycling station, and two upper limb stations.

Although FIG. 3 illustrates an example robotic rehabilitation system 300, various other types of robotic rehabilitation systems can be used in physical rehabilitation training, and any appropriate type of robotic rehabilitation system can be used in the systems and methods described in this specification. FIG. 3 also illustrates an example of different end-effectors used on the robotic motion machine 302, 304, and 306. In some embodiments the end-effectors may be designed to be re-configurable to allow users to be use the same motion machine to train the upper arm in a variety of ways. In some examples, the end-effectors may be designed to train the lower-limb in a variety of ways. In some examples, the diagnosis of the user will influence this versatility and choice of end-effectors. In some examples, the end-effectors may be instrumented with sensors to provide information on the interaction.

In some examples, the control system 112 within an example robotic rehabilitation system 300 where multiple players are being treated can be configured to provide assistive and resistive haptic feedback to one user's 104 robotic motion machine 302 based on another user's action on their robotic motion machine 304 during collaborative or cooperative multiplayer use.

In some examples, the control system 112 within an example robotic rehabilitation system 300 where multiple players are being treated can be configured to provide perturbations via the haptic feedback to one user's 104 robotic motion machine 302 based on another user's action on their robotic motion machine 304 during competitive multiplayer use.

Figure 4:
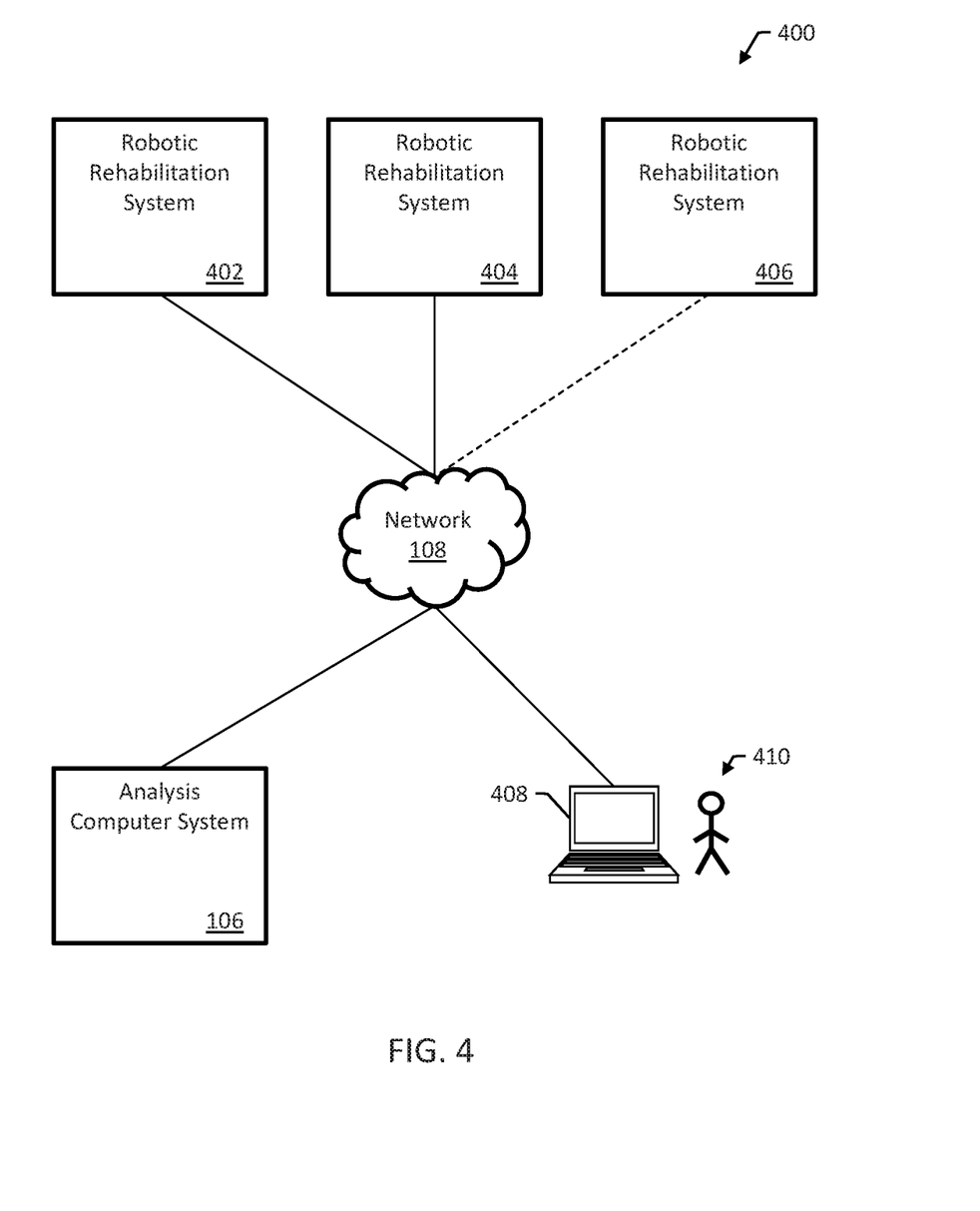
FIG. 4 illustrates an example network environment including multiple robotic rehabilitation systems.

FIG. 4 illustrates an example network environment 400 including multiple robotic rehabilitation systems 402, 404, and 406. Analysis computer system 106 can be configured to receive user interaction data from each of the robotic rehabilitation systems 402, 404, and 406. For example, analysis computer system 106 may receive user interaction data from some of the robotic rehabilitation systems 402 and 404 in real-time or near real-time and some other robotic rehabilitation systems 406 on a periodic basis or other basis depending on network availability.

Analysis computer system 106 can perform data analytics on aggregated user interaction data. Analysis computer system 106 can be configured as a server to present resulting analytics data on a user device 408 to, e.g., a physical rehabilitation therapist 410. For example, analysis computer system 106 may provide a graphical user interface (GUI) to the user device 408 as, e.g., a web page, for displaying resulting analytics data. User device 408 can be any appropriate computing device with a display, at least one processor, and a user input device; for example, user device 408 can be a laptop, tablet, or mobile phone.

Figure 5A:
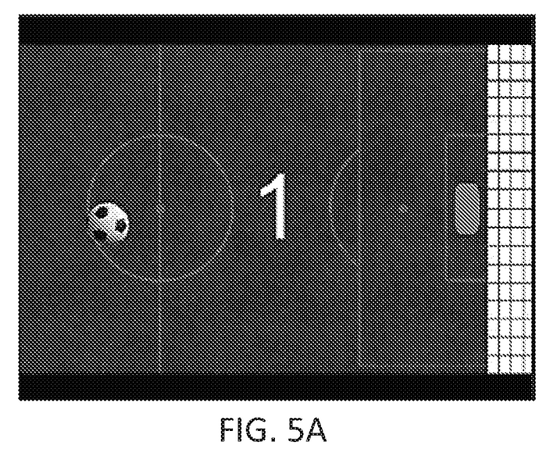
FIGS. 5A-C illustrate screen shots of an example display at a control system of a robotic rehabilitation system for interactive gaming.
Figure 5B:
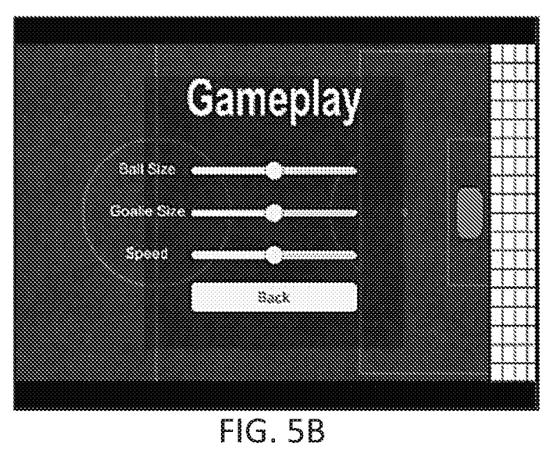
Figure 5C:
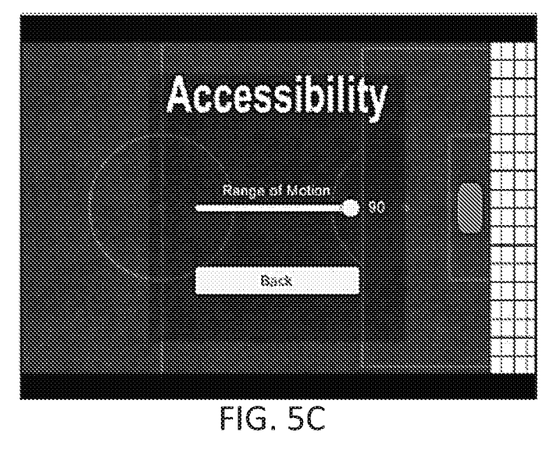

FIGS. 5A-C illustrate screen shots of an example display at a control system of a robotic rehabilitation system for interactive gaming. FIG. 5A shows a gameplay screen, FIG. 5B shows a game parameter adjustment screen, and FIG. 5C shows an accessibility adjustment screen.

In general, technologies at each station of a robotic rehabilitation system can be used to play the game regardless of the current physical setup at each station. The game can be customizable to different input settings and the physical and/or cognitive ability of the user, e.g., so that the game is more challenging for users further along in a physical therapy training program. In some examples, the game is configured for individual and community play, and the game may be competitive or cooperative in play. The motor and cognitive difficulty of the games can be personalized for each patient and during the sessions.

Typically, the game is interactive with the robotic motion machines. The game can accept position sensor information and force sensor data, and the game can then provide desired positions to robot controllers. In the example illustrated in FIGS. 5A-C, a user controls a "goalie" that is constrained horizontally and movable by the user up and down, and the aim of the game is to block soccer balls coming from the left hand side of the screen before they reach the goal on the right. In some examples, the gaming can be modified by sensors worn by the patient (e.g., by usage of biometric sensors).

Figure 6:
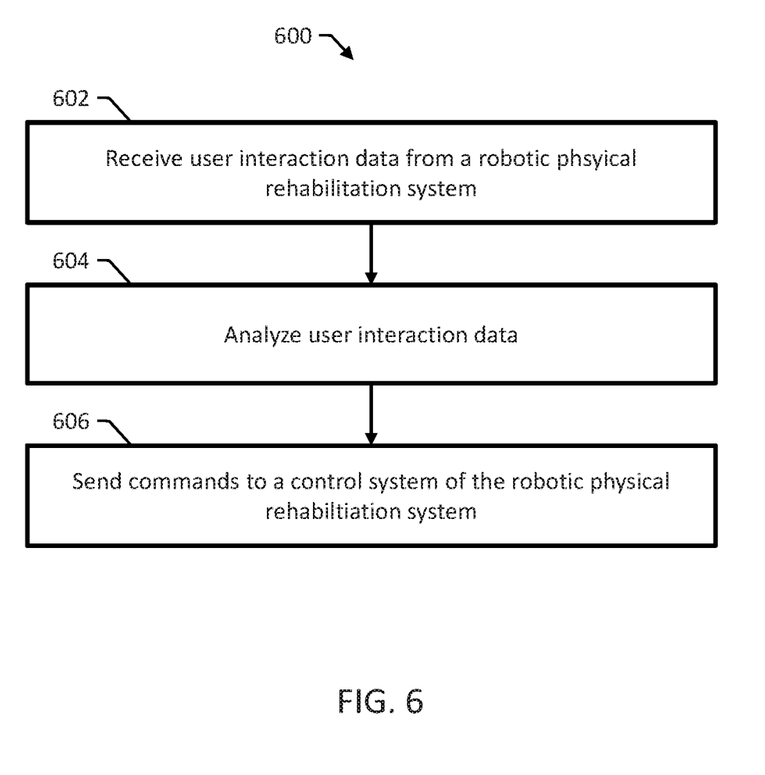
FIG. 6 is a flow diagram of an example method for analyzing robotic physical rehabilitation systems.

FIG. 6 is a flow diagram of an example method 600 for analyzing robotic physical rehabilitation systems. Method 600 includes receiving, by a robotic rehabilitation analyzer implemented on one or more processors, user interaction data characterizing a user's interaction with a robotic rehabilitation system (602). Method 600 includes analyzing, by the robotic rehabilitation analyzer, the user interaction data to track the user's past course of treatment and determine an action for the user's future course of treatment (604). Method 600 includes sending, by the robotic rehabilitation analyzer, one or more commands to the control system of the robotic rehabilitation system based on the action for the user's future course of treatment (606).

Although specific examples and features have been described above, these examples and features are not intended to limit the scope of the present disclosure, even where only a single example is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed in this specification (either explicitly or implicitly), or any generalization of features disclosed, whether or not such features or generalizations mitigate any or all of the problems described in this specification. Accordingly, new claims may be formulated during prosecution of this application (or an application claiming priority to this application) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A method for analyzing robotic physical rehabilitation systems, the method comprising:

receiving, by a robotic rehabilitation analyzer implemented on one or more processors, user interaction data characterizing a user's interaction with a robotic rehabilitation system comprising one or more robotic motion machines, a control system for controlling motors of the robotic motion machines, and one or more sensors for collecting the user interaction data while the user performs physical rehabilitation training using the one or more robotic motion machines;

analyzing, by the robotic rehabilitation analyzer, the user interaction data to track the user's past course of treatment and determine an action for the user's future course of treatment; and sending, by the robotic rehabilitation analyzer, one or more commands to the control system of the robotic rehabilitation system based on the action for the user's future course of treatment;

wherein the robotic rehabilitation system is a multi-user robotic physical rehabilitation gym comprising a plurality of component stations each comprising component robotic motion machines; and wherein sending one or more commands to the control system of the robotic rehabilitation system includes causing the control system of the robotic rehabilitation system to provide assistive and resistive haptic feedback to the one or more robotic motion machines based on a different user's action on a different robotic motion machine operated by the different user during collaborative or cooperative multiplayer use; and wherein the control system comprises a display and one or more processors configured for interactive gaming with the user while the user performs physical rehabilitation training, and wherein sending one or more commands to the control system comprises sending one or more commands to alter the interactive gaming with the user; and wherein the control system is configured for providing perturbations via haptic feedback to a first robotic motion machine of a first user based on a second user's action on a second robotic motion machine during competitive multiplayer use.

2. The method of claim 1, comprising receiving additional user interaction data from a plurality of additional users that perform physical rehabilitation training using the one or more robotic motion machines, wherein analyzing the user interaction data comprises analyzing the user interaction data and the additional user interaction data.

3. The method of claim 1, comprising receiving additional user interaction data from a plurality of additional robotic rehabilitation systems, wherein analyzing the user interaction data comprises analyzing the user interaction data and the additional user interaction data.

4. The method of claim 1, wherein the control system comprises a display and one or more processors configured to provide feedback to the user using the display, and wherein sending one or more commands to the control system comprises sending one or more commands to alter the feedback provided to the user using the display.

5. The method of claim 1, wherein the control system is configured for providing assistive and resistive haptic feedback to the user by controlling motors of the robotic motion machines, and wherein sending one or more commands to the control system comprises sending one or more commands to alter the assistive and resistive haptic feedback.

6. The method of claim 1, wherein analyzing the user interaction data comprises determining diagnosis data or therapy data or both for the user based on the user interaction data and comparison data.

7. The method of claim 1, wherein analyzing the user interaction data comprises determining, using comparison data, one or more of: error data, rate of learning data, data from biometric sensors, and force data.

8. The method of claim 1, comprising storing the user interaction data in a database storing additional interaction data from a plurality of other users and a plurality of other rehabilitation control systems and performing data analytics on aggregated data stored in the database.

9. A system for analyzing robotic physical rehabilitation systems, the system comprising:

one or more processors; and a robotic rehabilitation analyzer implemented on the one or more processors and configured to perform operations comprising:

receiving user interaction data characterizing a user's interaction with a robotic rehabilitation system comprising one or more robotic motion machines, a control system for controlling motors of the robotic motion machines, and one or more sensors for collecting the user interaction data while the user performs physical rehabilitation training using the one or more robotic motion machines;

analyzing the user interaction data to track the user's past course of treatment and determine an action for the user's future course of treatment; and sending one or more commands to the control system of the robotic rehabilitation system based on the action for the user's future course of treatment;

wherein the robotic rehabilitation system is a multi-user robotic physical rehabilitation gym comprising a plurality of component stations each comprising component robotic motion machines; and wherein sending one or more commands to the control system of the robotic rehabilitation system includes causing the control system of the robotic rehabilitation system to provide assistive and resistive haptic feedback to the one or more robotic motion machines based on a different user's action on a different robotic motion machine operated by the different user during collaborative or cooperative multiplayer use; and wherein the control system comprises a display and one or more processors configured for interactive gaming with the user while the user performs physical rehabilitation training, and wherein sending one or more commands to the control system comprises sending one or more commands to alter the interactive gaming with the user; and wherein the control system is configured for providing perturbations via haptic feedback to a first robotic motion machine of a first user based on a second user's action on a second robotic motion machine during competitive multiplayer use.

10. The system of claim 9, the operations comprising receiving additional user interaction data from a plurality of additional users that perform physical rehabilitation training use the one or more robotic motion machines, wherein analyzing the user interaction data comprises analyzing the user interaction data and the additional user interaction data.

11. The system of claim 9, the operations comprising receiving additional user interaction data from a plurality of additional robotic rehabilitation systems, wherein analyzing the user interaction data comprises analyzing the user interaction data and the additional user interaction data.

12. The system of claim 9, wherein the control system comprises a display and one or more processors configured to provide feedback to the user using the display, and wherein sending one or more commands to the control system comprises sending one or more commands to alter the feedback provided to the user using the display.

13. The system of claim 9, wherein the control system is configured for providing assistive and resistive haptic feedback to the user by controlling motors of the robotic motion machines, and wherein sending one or more commands to the control system comprises sending one or more commands to alter the assistive and resistive haptic feedback.

14. The system of claim 9, wherein the control system comprises a display and one or more processors configured for interactive gaming with the user while the user performs physical rehabilitation training, and wherein sending one or more commands to the control system comprises sending one or more commands to alter the interactive gaming with the user.

15. The system of claim 9, wherein analyzing the user interaction data comprises determining diagnosis data or therapy data or both for the user based on the user interaction data and comparison data.

16. The system of claim 9, wherein analyzing the user interaction data comprises determining, using comparison data, one or more of: error data, rate of learning data, data from biometric sensors, and force data.

17. The system of claim 9, the operations comprising storing the user interaction data in a database storing additional interaction data from a plurality of other users and a plurality of other rehabilitation control systems and performing data analytics on aggregated data stored in the database.

18. A non-transitory computer readable medium storing executable instructions that when executed by at least one processor of a computer control the computer to perform operations comprising:

receiving user interaction data characterizing a user's interaction with a robotic rehabilitation system comprising one or more robotic motion machines, a control system for controlling motors of the robotic motion machines, and one or more sensors for collecting the user interaction data while the user performs physical rehabilitation training using the one or more robotic motion machines;

analyzing the user interaction data to track the user's past course of treatment and determine an action for the user's future course of treatment; and sending one or more commands to the control system of the robotic rehabilitation system based on the action for the user's future course of treatment;

wherein the robotic rehabilitation system is a multi-user robotic physical rehabilitation gym comprising a plurality of component stations each comprising component robotic motion machines; and wherein sending one or more commands to the control system of the robotic rehabilitation system includes causing the control system of the robotic rehabilitation system to provide assistive and resistive haptic feedback to the one or more robotic motion machines based on a different user's action on a different robotic motion machine operated by the different user during collaborative or cooperative multiplayer use; and wherein the control system comprises a display and one or more processors configured for interactive gaming with the user while the user performs physical rehabilitation training, and wherein sending one or more commands to the control system comprises sending one or more commands to alter the interactive gaming with the user; and wherein the control system is configured for providing perturbations via haptic feedback to a first robotic motion machine of a first user based on a second user's action on a second robotic motion machine during competitive multiplayer use.

\* \* \* \* \*